(12) United States Patent
Lemmerhirt et al.

(10) Patent No.: US 7,888,709 B2
(45) Date of Patent: Feb. 15, 2011

(54) CAPACITIVE MICROMACHINED ULTRASONIC TRANSDUCER AND MANUFACTURING METHOD

(75) Inventors: David F. Lemmerhirt, Ann Arbor, MI (US); Collin A. Rich, Ypsilanti, MI (US)

(73) Assignee: Sonetics Ultrasound, Inc., Ann Arbor, MI (US)

( * ) Notice: Subject to any disclaimer, the term of this patent is extended or adjusted under 35 U.S.C. 154(b) by 0 days.

(21) Appl. No.: 12/420,683

(22) Filed: Apr. 8, 2009

(65) Prior Publication Data

US 2009/0250729 A1    Oct. 8, 2009

Related U.S. Application Data

(63) Continuation-in-part of application No. 11/612,656, filed on Dec. 19, 2006.

(51) Int. Cl.
*H01L 29/84* (2006.01)
(52) U.S. Cl. .................. 257/254; 257/E25.029; 257/E21.158
(58) Field of Classification Search .......... 257/254, 257/E25.029, E21.158
See application file for complete search history.

(56) References Cited

U.S. PATENT DOCUMENTS

| | | | |
|---|---|---|---|
| 4,906,837 | A | 3/1990 | Doneen et al. |
| 4,936,649 | A | 6/1990 | Lymer et al. |
| 5,873,830 | A | 2/1999 | Hossack et al. |
| 5,921,933 | A | 7/1999 | Sarkis et al. |
| 6,106,472 | A | 8/2000 | Chiang et al. |
| 6,142,946 | A | 11/2000 | Hwang et al. |
| 6,246,158 | B1 | 6/2001 | Ladabaum |
| 6,251,075 | B1 | 6/2001 | Hashimoto |
| 6,280,704 | B1 | 8/2001 | Schutt et al. |
| 6,314,057 | B1 | 11/2001 | Solomon et al. |
| 6,320,239 | B1 | 11/2001 | Eccardt et al. |
| 6,328,696 | B1 | 12/2001 | Fraser |
| 6,342,891 | B1 | 1/2002 | Fenster et al. |
| 6,375,617 | B1 | 4/2002 | Fraser |
| 6,428,469 | B1 | 8/2002 | Iddan et al. |
| 6,458,084 | B2 | 10/2002 | Tsao et al. |
| 6,506,156 | B1 | 1/2003 | Jones et al. |
| 6,506,160 | B1 | 1/2003 | Van Stralen et al. |

(Continued)

FOREIGN PATENT DOCUMENTS

EP    666483    1/1995

(Continued)

OTHER PUBLICATIONS

U.S. Appl. No. 12/727,143, filed Mar. 18, 2010, David F. Lemmerhirt.

(Continued)

*Primary Examiner*—Tan N Tran
(74) *Attorney, Agent, or Firm*—Jeffrey Schox

(57) ABSTRACT

The integrated circuit/transducer device of the preferred embodiment includes a substrate, a complementary-metal-oxide-semiconductor (CMOS) circuit that is fabricated on the substrate, and a capacitive micromachined ultrasonic transducer (cMUT) element that is also fabricated on the substrate. The CMOS circuit and cMUT element are fabricated during the same foundry process and are connected. The cMUT includes a lower electrode, an upper electrode, a membrane structure that support the upper electrode, and a cavity between the upper electrode and lower electrode.

11 Claims, 9 Drawing Sheets

U.S. PATENT DOCUMENTS

| | | | |
|---|---|---|---|
| 6,540,981 B2 | 4/2003 | Klaveness et al. | |
| 6,546,279 B1 | 4/2003 | Bova et al. | |
| 6,547,731 B1 | 4/2003 | Coleman et al. | |
| 6,562,650 B2 | 5/2003 | Ladabaum | |
| 6,605,043 B1 | 8/2003 | Dreshel et al. | |
| 6,610,012 B2 | 8/2003 | Mault | |
| 6,667,245 B2 | 12/2003 | Chow et al. | |
| 6,939,531 B2 | 9/2005 | Schutt et al. | |
| 7,030,536 B2 * | 4/2006 | Smith et al. | 310/309 |
| 2003/0032211 A1 * | 2/2003 | Ladabaum | 438/42 |
| 2003/0163046 A1 | 8/2003 | Nohara et al. | |
| 2003/0216621 A1 | 11/2003 | Alpert et al. | |
| 2004/0006273 A1 | 1/2004 | Kim et al. | |
| 2004/0225220 A1 | 11/2004 | Rich | |
| 2005/0033177 A1 | 2/2005 | Rogers | |
| 2006/0058667 A1 | 3/2006 | Lemmerhirt et al. | |
| 2007/0038088 A1 | 2/2007 | Rich et al. | |
| 2007/0167811 A1 | 7/2007 | Lemmerhirt et al. | |
| 2007/0167812 A1 | 7/2007 | Lemmerhirt et al. | |
| 2008/0071149 A1 | 3/2008 | Rich | |
| 2008/0071292 A1 | 3/2008 | Rich | |
| 2009/0250729 A1 | 10/2009 | Lemmerhirt et al. | |

FOREIGN PATENT DOCUMENTS

| | | |
|---|---|---|
| EP | 936144 | 8/1999 |
| GB | 2272762 | 5/1994 |
| JP | 2000-347072 | 12/2000 |

OTHER PUBLICATIONS

Rafael Nadal-Guardia et al., "Constant Charge Operation of Capacitor Sensors Based on Switched-Current Circuits", IEEE Sensors Journal, vol. 3, No. 6 Dec. 2003.

E. Cianci et al., "Improvements towards a reliable fabrication process for cMUT", Microelectronic Engineering 67-68 (2003) 602-608.

Ecardt, Peter and Kurt Niederer, "Micromachined ultrasound transducers with improved coupling factors from a CMOS compatible process", Ultrasonics 38 (2000) 774-780.

Westberg, David et al. "Surface micromaching by sacrificial aluminium etching", J. Micromech, Microeng. 6 (1996) 376-384. Printed in the UK.

International Search Report, PCT/US2004/028326, Mailed Oct. 12, 2004.

Masoliver, Michael, "Concrete That Lets in Light" Insight, Mar. 2000, pp. 18 and 19.

Glassman, Mark, "Concrete is Learning New Tricks, Like Letting in the Light", The New York Times, Aug. 10, 2004.

* cited by examiner

CAPACITIVE MICROMACHINED ULTRASONIC TRANSDUCER AND MANUFACTURING METHOD

CROSS-REFERENCE TO RELATED APPLICATIONS

The present invention claims priority as a continuation-in-part of U.S. Ser. No. 11/612,656 filed on 19 Dec. 2006 and entitled "Capacitive Micromachined Ultrasound Transducer", which claims priority as a continuation-in-part of U.S. Ser. No. 11/229,197 filed on 15 Nov. 2005 and titled "Integrated Circuit for an Ultrasound System", which claims priority to the following three provisional applications: U.S. Provisional Patent Application No. 60/610,320 filed 15 Sep. 2004 and titled "Beamforming", U.S. Provisional Patent Application No. 60/610,319 filed 15 Sep. 2004 and titled "Transducer", and U.S. Provisional Patent Application No. 60/610,337 filed 15 Sep. 2004 and titled "Electronics". Each of the five applications (the two applications and the three provisional applications) are incorporated in their entirety by this reference.

TECHNICAL FIELD

The present invention relates generally to the field of semiconductor design and manufacture, and more particularly to the field of capacitive micromachined ultrasonic transducers.

BACKGROUND

Historically, transducer elements of ultrasonic imaging devices have employed piezoelectric transducers to receive and transmit acoustic signals at ultrasonic frequencies. The performance of piezoelectric transducers is limited by their narrow bandwidth and acoustic impedance mismatch to air, water, and tissue. In an attempt to overcome these limitations, current research and development has focused on the production of capacitive micromachined ultrasonic transducer (cMUT) elements. cMUT elements generally include at least a pair of electrodes separated by a uniform air or vacuum gap, with the upper electrode suspended on a flexible membrane. Impinging acoustic signals cause the membrane to deflect, resulting in capacitive changes between the electrodes, which produce electronic signals usable for ultrasonic imaging.

The nature of the signals produced by cMUT elements demands that they are located as close as possible to the electronic readout circuits, ideally on the same physical substrate. While there have been efforts to make cMUT elements compatible with complementary metal-oxide (CMOS) integrated circuits, the conventional approaches have relied on depositing and patterning layers to form cMUT structures after the CMOS process steps are complete. These approaches raise substantial financial and technical barriers due to the high cost of adding patterned layers to a finely-tuned CMOS process and due to the high process temperatures needed to deposit the high quality structural layers needed for micromachined devices. The production of a cMUT element using this approach may require temperatures higher than 500 degrees Celsius., at which point the metallization layers within the CMOS circuit elements may begin to form hillocks or to alloy with adjacent layers. These phenomena may render the integrated circuit non-functional or, at best, will severely reduce production yield. In short, the existing approaches have failed to viably integrate the ultrasonic functions of a cMUT into an integrated circuit.

Thus, there is a need in the art of ultrasonic imaging devices for a new and improved capacitive micromachined ultrasonic transducer. This invention provides a design and manufacturing method for such transducer device.

DESCRIPTION OF THE PREFERRED EMBODIMENT

The following description of the preferred embodiment of the invention is not intended to limit the invention to this preferred embodiment, but rather to enable any person skilled in the art of medical devices to make and use this invention.

Figure 1:
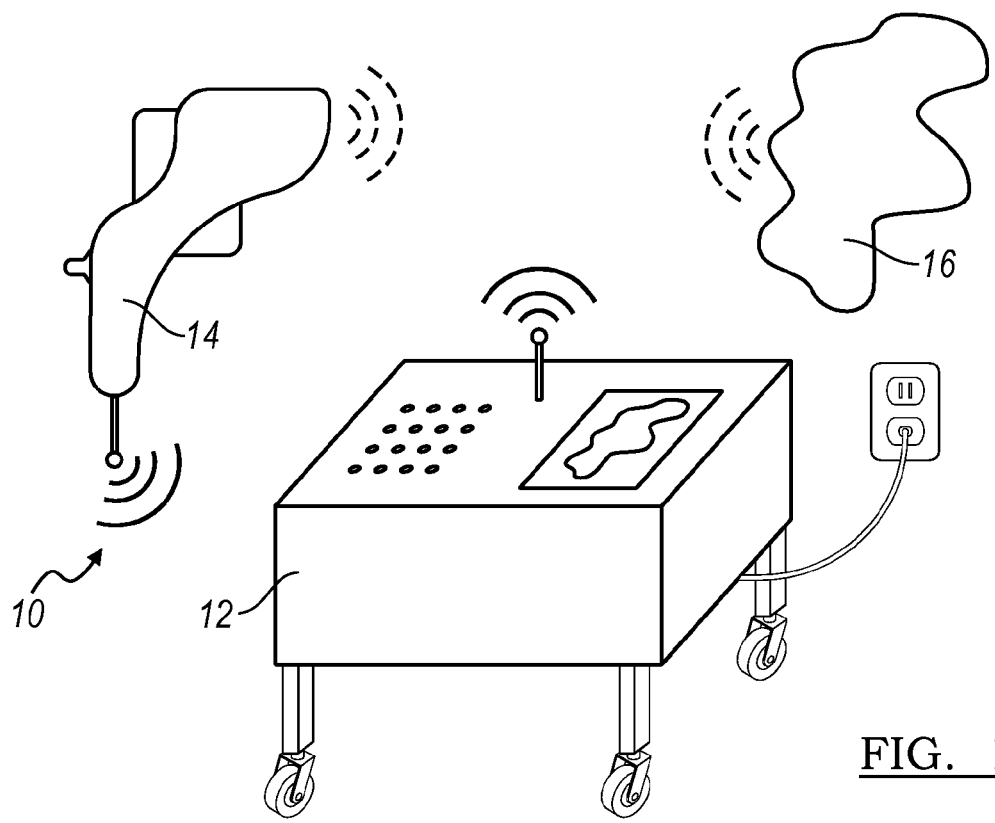
FIG. 1 is a representation of an ultrasound system of the preferred embodiment.

The ultrasound system 10 of the preferred embodiment, as shown in FIG. 1, includes a central console 12 and a handheld probe 14 with an integrated circuit/transducer device. The handheld probe 14 is adapted to receive a wireless beam signal from the central console 12, generate an ultrasonic beam, detect an ultrasonic echo at multiple locations, combine the ultrasonic echoes into a single multiplexed echo signal, and transmit a multiplexed echo signal to the central console 12. The ultrasound system 10 provides an improved ultrasound system that collects enough echo data for 3D imaging and that transmits the echo data by a wireless link to overcome the limitations and drawbacks of typical ultrasound systems.

The ultrasound system 10 has been specifically designed to allow medical specialists to view the anatomy and pathologic conditions of a patient. The ultrasound system 10 may, however, be used to view any subject 16 that at least partially reflects ultrasound beams. Such non-medical uses may include ultrasonic microscopy, non-destructive testing, and other situations that would benefit from a volumetric imaging of the subject 16.

1. Central Console

Figure 2:
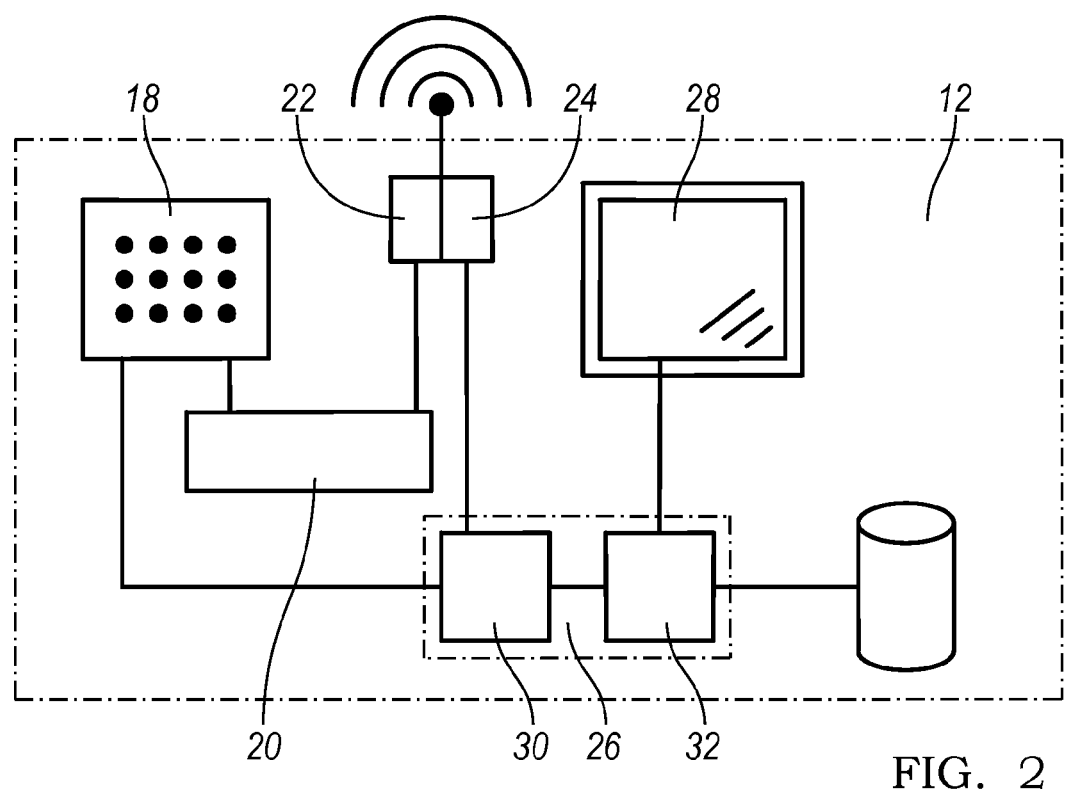
FIG. 2 is a schematic representation of the central console of the ultrasound system.

The central console 12 of the preferred embodiment functions to: provide interaction with the operator of the ultrasound system 10; wirelessly communicate with the handheld probe 14; control the ultrasonic beams of the handheld probe 14; process the 3D images from the multiplexed echo signals of the handheld probe 14; and display a 3D image. The central console 12 may further provide other functions, such as providing data storage, data compression, image printouts, format conversions, communication links to a network, or any other appropriate function. To accomplish the five main functions, the central console 12 is conceptually separated into console controls 18, a beam controller 20, a console transmitter 22 and console receiver 24, an image processor 26, and a console display 28, as shown in FIG. 2. The central console 12 is preferably designed as a mobile unit (such as a wheeled cart or a laptop computer), but may alternatively be designed as a fixed unit (such as a cabinet structure).

The console controls 18 of the central console 12 provide interaction with the operator of the ultrasound system 10. The console controls 18 preferably allow the operator to configure the ultrasound system 10, to switch between imaging modes, and to capture frame/cine. The console controls 18 may alternatively provide other appropriate functions. Input from the operator is collected, parsed, and sent to the image processor 26 and/or the beam controller 20 as appropriate. The console controls 18 may include knobs, dials, switches, buttons, touch pads, fingertip sensors, sliders, joysticks, keys, or any other appropriate device to provide interaction with the operator.

The beam controller 20 of the central console 12 controls the ultrasonic beams of the handheld probe 14. The operator of the ultrasound system 10, through the console controls 18 described above, may select a particular imaging mode (e.g., 3D, 2D slice, or local image zoom) for a subject 16. To comply with this selection, the beam controller 20 preferably creates a beam signal that adjusts or modulates the frequency, sampling rate, filtering, phasing scheme, amplifier gains, transducer bias voltages, and/or multiplexer switching of the handheld probe 14. Alternatively, the beam controller 20 may create two or more signals that adjust or modulate these parameters. Further, the beam controller 20 may create a beam signal that adjusts or modulates other appropriate parameters of the handheld probe 14.

The console transmitter 22 and the console receiver 24 of the central console 12 function to provide a wireless communication link with the handheld probe 14. Specifically, the console transmitter 22 functions to transmit beam signals to the handheld probe 14, while the console receiver 24 functions to receive echo signals from the handheld probe 14. In the preferred embodiment, the console transmitter 22 and the console receiver 24 use radiofrequency (RF) communication and an appropriate protocol with a high data throughput. In an alternative embodiment, however, the console transmitter 22 and the console receiver 24 may use infrared or other high-speed optical communication instead of, or in addition to, RF communication. The console transmitter 22 and the console receiver 24 may incorporate frequency hopping, spread-spectrum, dual-band, encryption, and/or other specialized transmission techniques known in the art to ensure data security and/or integrity in noisy environments. In the preferred embodiment, the console transmitter 22 and the console receiver 24 are located within different housings and are operated at different frequencies. In an alternative embodiment, the console transmitter 22 and the console receiver 24 may be combined (as a console transceiver) and/or may operate within the same channel or frequency.

The image processor 26 of the central console 12, which functions to construct 3D images from the multiplexed echo signals of the handheld probe 14, is preferably composed of a frame compiler 30 and an image engine 32. The frame compiler 30 of the image processor 26 functions to assemble a single 3D image (or 3D frame) from the multiplexed echo signals of the handheld probe 14. The echo signals, which are a series of pulses with specific time, amplitude, and phasing information, are correlated, summed, and transformed into voxels for the 3D image. Noise reduction, phase deaberration, contrast enhancement, orthogonal compounding, and other operations are also performed at this stage. In the preferred embodiment, as much as possible, these operations are performed in parallel fashion with dedicated algorithms, thus allowing the frame compiler 30 to be optimized for maximum speed. The frame compiler 30 preferably consists of a massively parallel set of lower-cost, medium-performance DSP cores, but may alternatively include other appropriate devices.

The image engine 32 of the image processor 26 receives complete frames from the frame compiler 30 and provides all higher-level processing (such as image segmentation) of the 3D frames. In the preferred embodiment, the image engine 32 also serves as a collection point for all echo data in the ultrasound system 10. The image engine 32 preferably consists of a high-performance, highly programmable DSP core, but may alternatively include other appropriate devices. In an alternative embodiment, the image processor 26 may include other appropriate devices to construct 3D images from the multiplexed echo signals of the handheld probe 14.

The console display 28 functions to present an image of the subject 16 to the operator in a form that facilitates easy and intuitive manipulation, navigation, measurement, and quantification. Examples of display modes include 3D, semi-transparent rendering, and 2D slices through the 3D structure. The console display 28 preferably includes a conventional LCD screen, but may alternatively include any appropriate device (such as a holographic or stereoscopic device) to present the scanned images.

2. Handheld Probe

Figure 3:
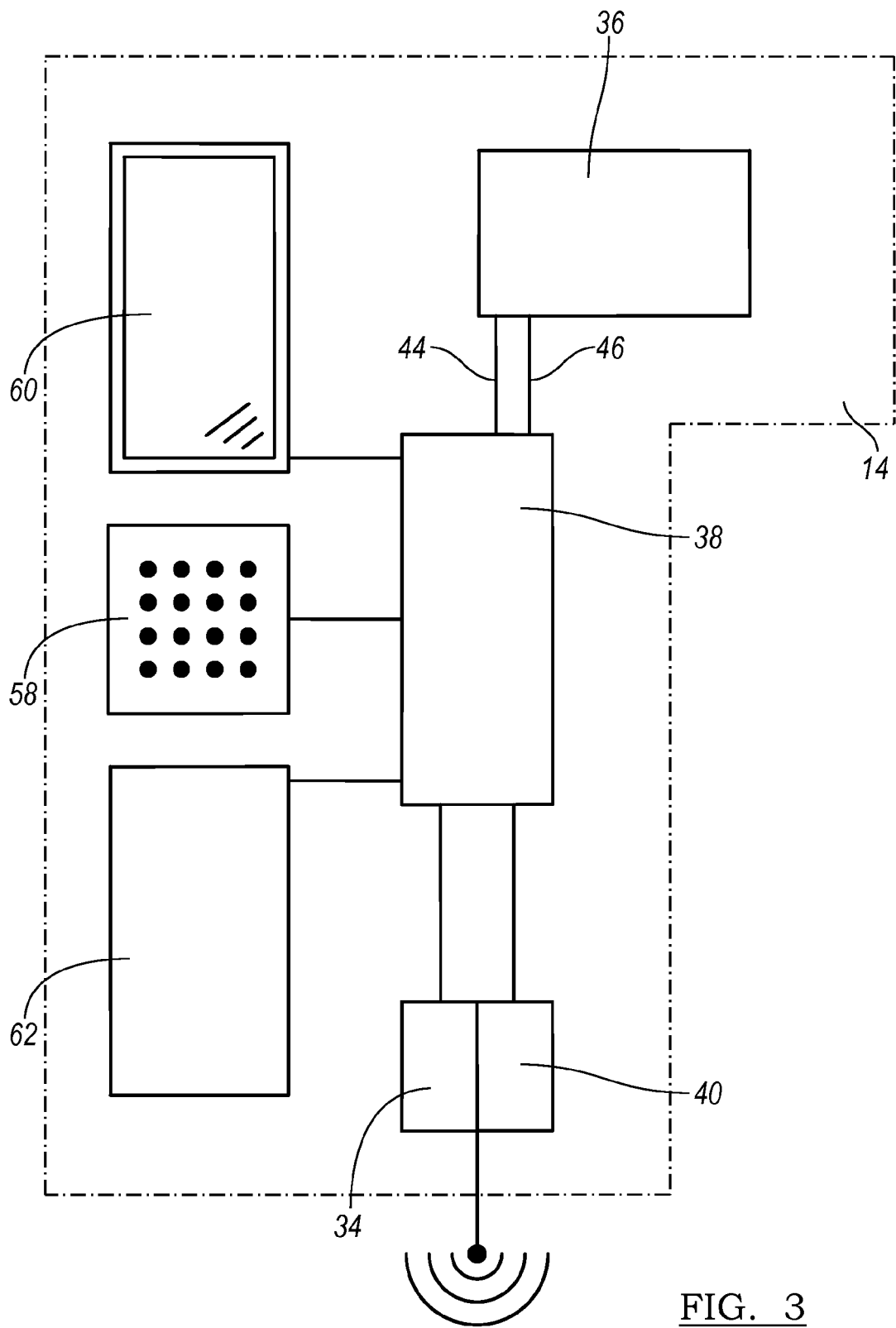
FIG. 3 is a schematic representation of a handheld probe for the ultrasound system.

The handheld probe 14 of the preferred embodiment functions to: wirelessly receive beam signals from the central console 12; generate an ultrasonic beam and detect an ultrasonic echo at multiple locations; combine the ultrasonic echoes into a single multiplexed echo signal; and wirelessly transmit the echo signals to the central console 12. The handheld probe 14 may further provide other functions, such as providing data storage, data compression, or any other appropriate function. To accomplish the four main functions, the central console 12 is conceptually separated into a probe receiver 34, a first integrated circuit/transducer device 36, a second integrated circuit 38, and a probe transmitter 40, as shown in FIG. 3.

The probe receiver 34 and the probe transmitter 40 of the handheld probe 14 function to provide a wireless communication link with the central console 12. Specifically, the probe receiver 34 functions to receive beam signals from the central console 12, while the probe transmitter 40 functions to transmit a multiplexed echo signal to the central console 12. The probe receiver 34 and the probe transmitter 40 use the same communication method and protocol as the console transmitter 22 and the console receiver 24. In the preferred embodiment, the probe receiver 34 and the probe transmitter 40 are located within different housings. In an alternative embodiment, the probe receiver 34 and the probe transmitter 40 may be combined (as a probe transceiver).

Figure 4:
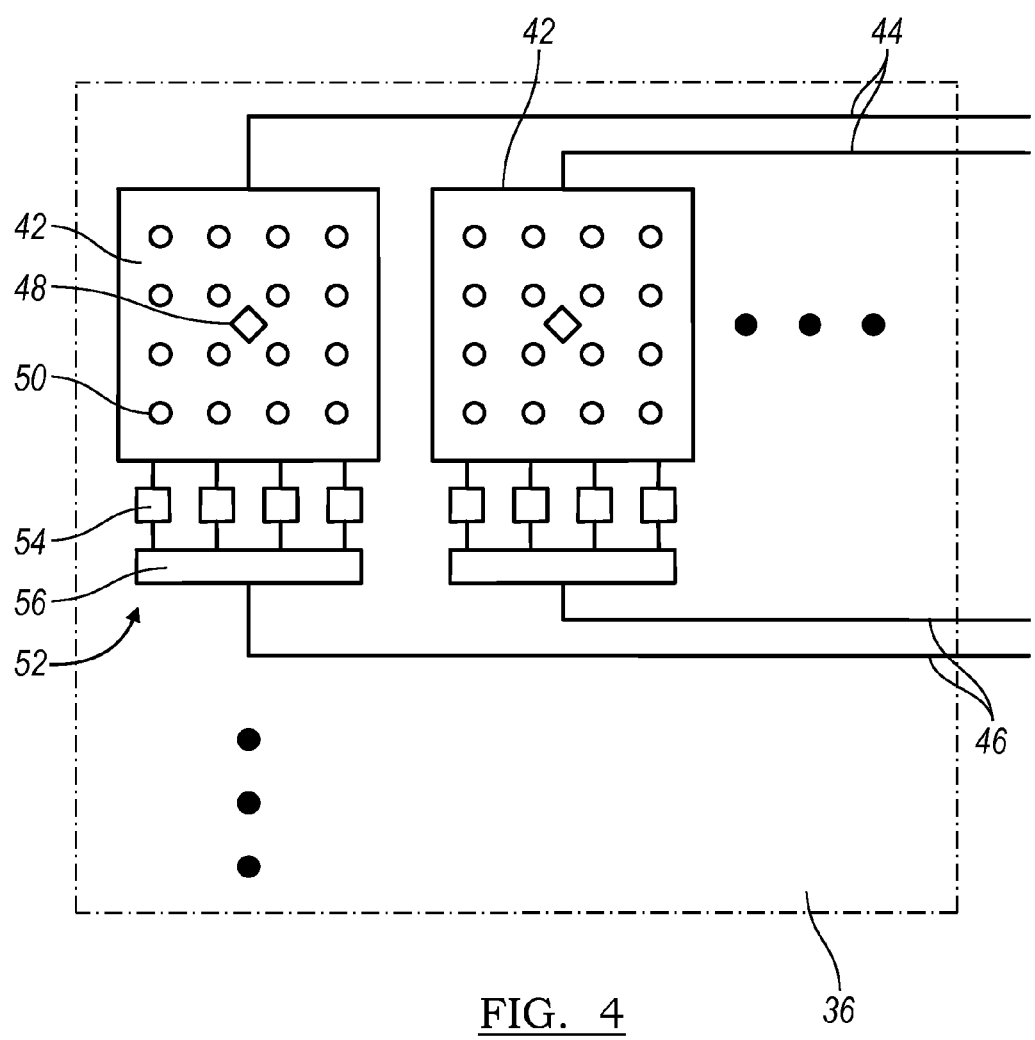
FIG. 4 is a schematic representation of a first example of an integrated circuit for the handheld probe.

The first integrated circuit/transducer device 36 of the handheld probe 14 functions to generate an ultrasonic beam, detect an ultrasonic echo at multiple locations, and to combine the ultrasonic echoes into multiplexed echo signals. The first integrated circuit/transducer device 36 preferably accomplishes these functions with the use of a 2D array of transducer cells 42, a series of beam-signal leads 44 that are adapted to carry the beam signals to the transducer cells 42, and a series of echo-signal leads 46 that are adapted to carry the multiplexed echo signals from the transducer cells 42, as shown in FIG. 4. The first integrated circuit/transducer device 36 may alternatively accomplish these functions with other suitable devices.

Figure 5:
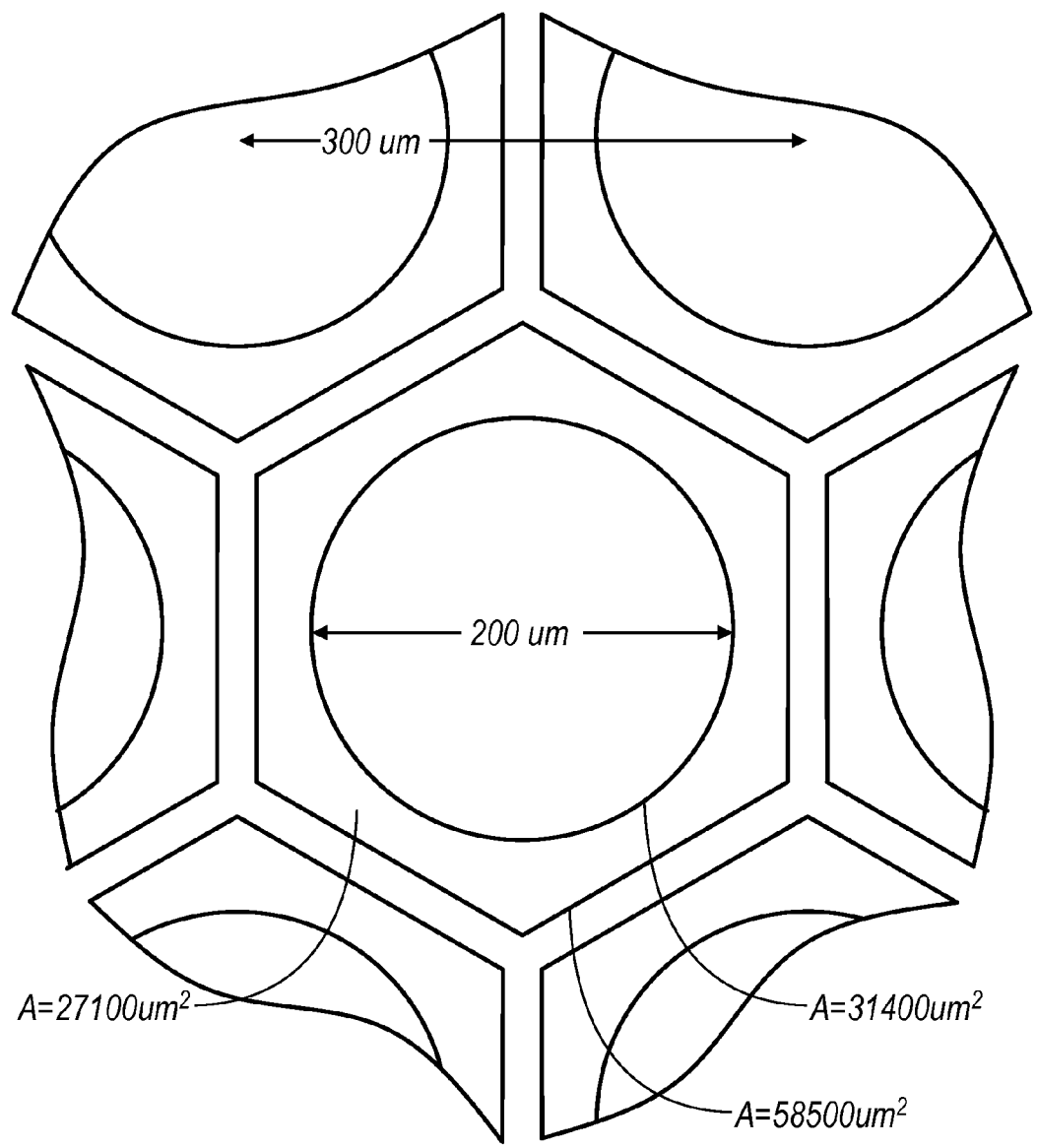
FIG. 5 is a representation of the relative size and proportion of the elements of the integrated circuit.

Each transducer cell 42 of the first integrated circuit/transducer device 36, which functions as a 2D phased subarray to scan one sector of the entire viewing field, preferably includes at least one ultrasonic beam generator 48, at least four (and preferably fifteen or sixteen) ultrasonic echo detectors 50, and at least one first multiplexer 52. The ultrasonic beam generator 48 and the ultrasonic echo detectors 50 of the transducer cell 42 function to generate an ultrasonic beam and to detect an ultrasonic echo at multiple locations, respectively. Preferably, the ultrasonic beam generator 48 and the ultrasonic echo detectors 50 are separate elements, which simplifies the front-end electronics for the first integrated circuit/transducer device 36 and allows the ultrasonic beam generator 48 and the ultrasonic echo detectors 50 to be separately optimized for their individual function. For example, the ultrasonic beam generator 48 may be optimized for high output (with increased ruggedness), while the ultrasonic echo detector 50 may be optimized for high sensitivity. This separate optimization may reduce edge wave effects (since a single point source can be fired instead of a complete subaperture). Although separate elements, the ultrasonic beam generator 48 and the ultrasonic echo detector 50 preferably share a basic shape and construction and preferably differ only by the diaphragm diameter, thickness, tensile stress, gap spacing, control electronics, and/or electrode configuration. Alternatively, the ultrasonic beam generator 48 and the ultrasonic echo detectors 50 may be formed as the same component (i.e., dual-function transducers). If the first integrated circuit/transducer device 36 is operating at 3 MHz, the ultrasonic beam generator 48 and the ultrasonic echo detectors 50 have a preferred diameter of 100-200 μm and a preferred pitch of approximately 250±50 μm, as shown in FIG. 5. The ultrasonic beam generator 48 and the ultrasonic echo detectors 50 may, however, have any suitable diameter and pitch.

The first multiplexer 52 of the transducer cell 42 functions to combine the ultrasonic echoes from the ultrasonic echo detectors 50 into a multiplexed echo signal. To collect enough echo data for 3D imaging, the first integrated circuit/transducer device 36 preferably includes at least 4,096 ultrasonic echo detectors 50, more preferably includes at least 15,360 ultrasonic echo detectors 50, and most preferably includes at least 16,384 ultrasonic echo detectors 50. From a manufacturing standpoint, the number of echo-signal leads 46 between the first integrated circuit/transducer device 36 and the second integrated circuit 38 is preferably equal to or less than 1024 connections, and more preferably equal to or less than 512 connections. Thus, the first multiplexer 52 preferably combines the echo signals at least in a 4:1 ratio. The first multiplexer 52 may use time division multiplexing (TDM), quadrature multiplexing, frequency division multiplexing (FDM), or any other suitable multiplexing scheme. Further, the first multiplexer 52 may actually be two multiplexers (indicated in FIG. 4 as a first portion 54 and a second portion 56) combined that either use the same or different multiplexing schemes.

In a first example of the preferred embodiment, as shown in FIG. 4, the transducer cell 42 is square shaped and the first integrated circuit/transducer device 36 includes 1,024 transducer cells 42 (preferably arranged in a square pattern with thirty-two transducer cells 42 along one dimension and thirty-two transducer cells 42 along another dimension). Preferably, each transducer cell 42 includes: sixteen ultrasound echo detectors 50 (plus one ultrasound beam generator 48 and one first multiplexer 52) in a transducer cell, and 1,024 transducer cells 42 in the first integrated circuit/transducer device 36. This arrangement provides a manageable level of echo-signal leads 46 to the second integrated circuit 38 (1,024 echo-signal leads), while providing enough echo data (16,384 ultrasonic echo detectors 50) for 3D image rendering. The first multiplexer 52, in this arrangement, combines sixteen echo signals into one multiplexed echo signal using a 16:1 TDM device. In a variation of this example, the first multiplexer 52 combines only four echo signals into one multiplexed echo signal using a 4:1 TDM device. Since there are four multiplexed echo signals and only one echo-signal lead, the first integrated circuit of this example performs four passes, each pass with a new beam signal and each pass with only $¼^{th}$ of the ultrasonic echo detectors 50 contributing to the echo signal. In this manner, the first multiplexer 52 is only combining a portion of the echo signals into a multiplexed signal.

Figure 6:
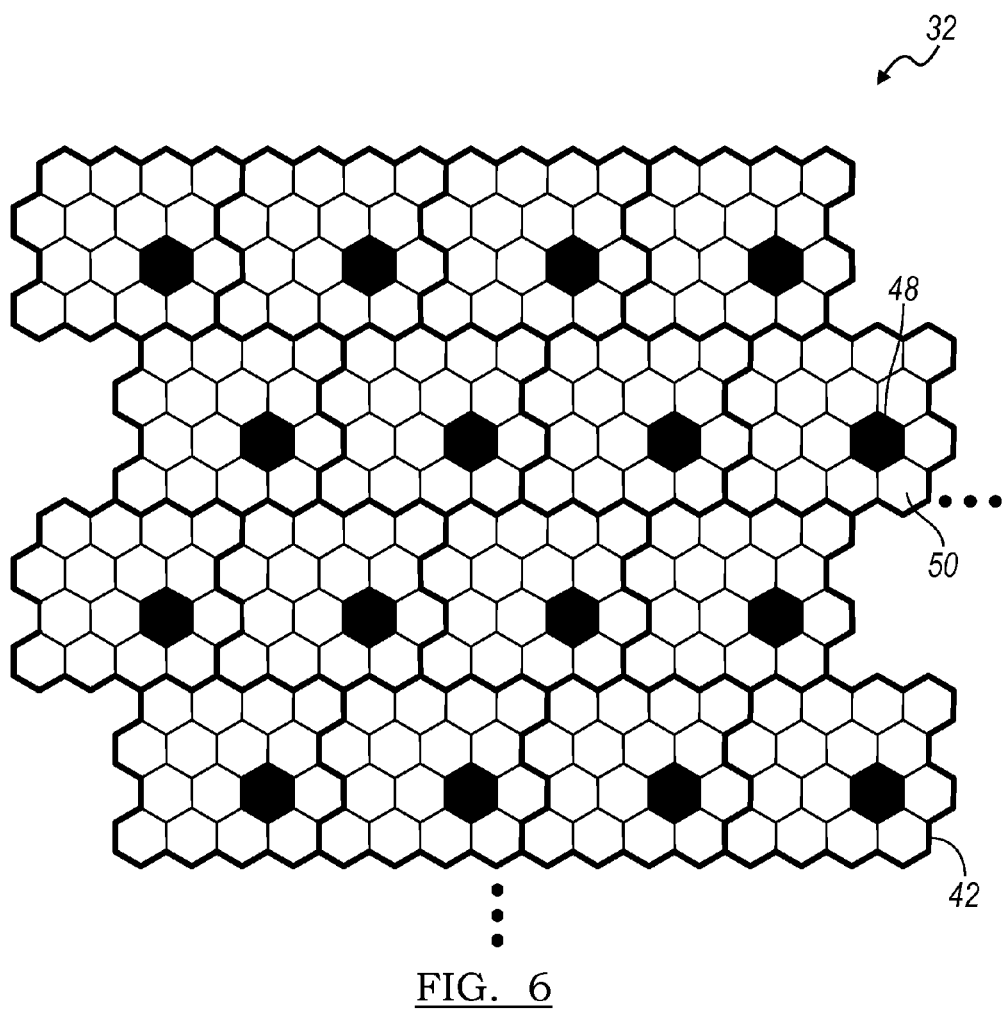
FIGS. 6 and 7 are schematic representations of two variations of a second example of an integrated circuit for the handheld probe.
Figure 7:
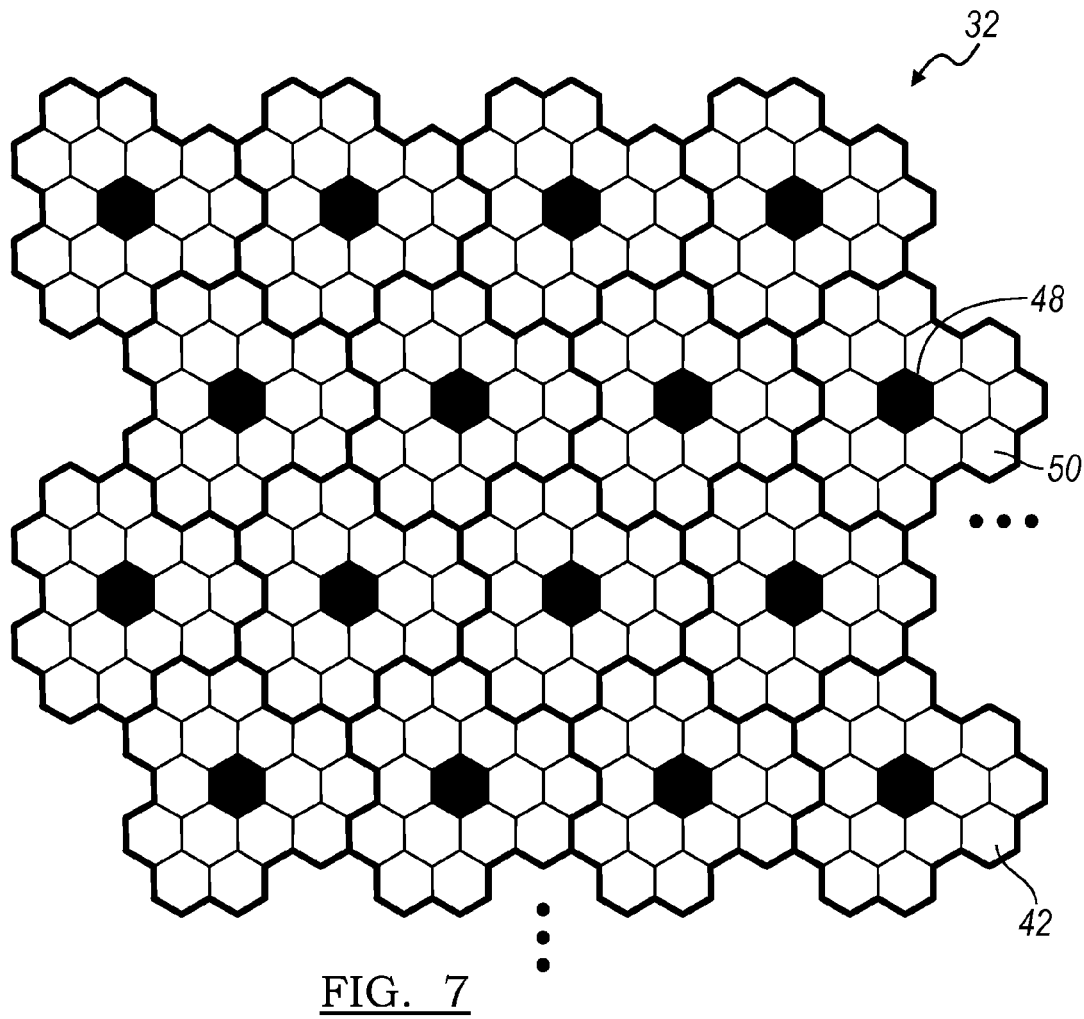

In a second example of the preferred embodiment, as shown in FIG. 6, the transducer cell 42 is roughly rectangular shaped and the first integrated circuit/transducer device 36 includes 1,024 transducer cells 42 (preferably arranged in a square pattern with thirty-two transducer cells 42 along one dimension and thirty-two transducer cells 42 along another dimension). Preferably, each roughly rectangular transducer cell 42 includes: one ultrasound beam generator 48 near the center, fifteen ultrasound echo detectors 50, and one first multiplexer (not shown). The ultrasound beam generators 48 are preferably arranged in a regular hexagonal tessellation, but may alternatively be arranged in any suitable pattern. This arrangement provides a manageable level of echo-signal leads to the second integrated circuit (1,024 echo-signal leads), while providing enough echo data (15,360 ultrasonic echo detectors 50) for 3D image rendering. The first multiplexer, in this arrangement, combines fifteen echo signals into one multiplexed echo signal using a 15:1 TDM device (potentially implemented as a 16:1 device, or as two 4:1 devices, with one repeated or null signal). In a variation of this second example, as shown in FIG. 7, the transducer cell 42 is roughly snowflake shaped. Preferably, each roughly snow-flaked shaped transducer cell 42 includes: one ultrasound beam generator 48 in the center, fifteen ultrasound echo detectors 50 (arranged as six "interior" ultrasound echo detectors 50 and nine "exterior" ultrasound echo detectors 50), and one first multiplexer (not shown).

Since the first integrated circuit/transducer device 36 is preferably limited to electronics that are essential to getting signals on- and off-chip, the first integrated circuit/transducer device 36 is preferably manufactured by a standard low-cost CMOS process at an existing foundry (e.g. AMI Semiconductor, 1.5 μm). The ultrasonic beam generator 48 and the ultrasonic echo detectors 50 are preferably microfabricated on the first integrated circuit/transducer device 36 as capacitive micro-machined ultrasonic transducers (cMUT), similar in structure and function to devices disclosed by U.S. Pat. No. 6,246,158 (which is incorporated in its entirety by this reference), but differing significantly in structural materials and manufacturing method as described in sections three and four below.

The second integrated circuit 38, as shown in FIG. 3, of the handheld probe 14 functions to receive and transmit the beam signals from the probe receiver 34 to the beam-signal leads 44 of the first integrated circuit/transducer device 36, and to receive and transmit the multiplexed echo signals from the echo-signal leads 46 to the probe transmitter 40. Preferably, the second integrated circuit 38 further conditions the multiplexed echo signals to facilitate wireless communication to the central console 12. The conditioning may include converting the analog echo signals to adequately sampled (e.g. above Nyquist) digital signals, amplifying the analog echo signals, compressing the digital echo signals, and performing an error-correction process on the echo signals. The conditioning may further include additional multiplexing of the multiplexed echo signals into one channel (or simply less channels). Any number of multiplexing schemes may be used, including time-division multiplexing, code-division multiplexing, frequency-division multiplexing, packet-based transmission, or any other suitable multiplexing scheme. The second integrated circuit 38 preferably uses conventional devices and manufacturing methods, but may alternatively use any suitable device and any suitable manufacturing method.

In the preferred embodiment, the handheld probe 14 further provides time gain compensation of the echo signals, which corrects for attenuation and allows objects at a greater depth to be clearly depicted with objects of lesser depth. This function may be integrated onto the first integrated circuit/transducer device 36, the second integrated circuit 38, or any other suitable locations within the handheld probe 14. In alternative embodiments, the problem of attenuation may be solved with other suitable devices, either within the handheld probe 14, the central console 12, or any other suitable location.

In the preferred embodiment, the central console 12 transmits multiple beam signals as a single multiplexed beam signal. For this reason, the central console 12 preferably includes a multiplexer (not shown) and the handheld probe 14 includes a de-multiplexer (not shown). In alternative embodiments, the beam signals are sent using multiple channels or using another suitable scheme.

In the preferred embodiment, the handheld probe 14 further includes probe controls 58, which function to provide additional interaction with the operator of the ultrasound system 10. Like the console controls 18, the probe controls 58 preferably allow the operator to configure the ultrasound system 10, to switch between imaging modes, and to capture frame/cine. Because of the proximity to the subject 16, however, the probe controls 58 may further include additional features, such as flag image, add caption or notation, add voice notation, and take measurement from image. The probe controls 58 may alternatively provide other appropriate functions. Input from the operator is collected, wirelessly transmitted to the central console 12, and routed to the image processor 26 and/or the beam controller 20 as appropriate. The probe controls 58 may include knobs, dials, switches, buttons, touch pads, fingertip sensors, sliders, joysticks, keys, or any other appropriate device(s) to provide interaction with the operator. The handheld probe 14 with the probe controls 58 of the preferred embodiment satisfies the need to allow operation of an ultrasound system 10 during a patient examination without requiring physical proximity to the central console 12.

In the preferred embodiment, the handheld probe 14 further includes a probe display 60. In a first variation of the preferred embodiment, the console transmitter 22 and the probe receiver 34 are further adapted to communicate information about the system configuration (such as imaging modes). With this variation, the probe display 60 is preferably adapted to display the system configuration. In a second variation of the preferred embodiment, the console transmitter 22 and the probe receiver 34 are further adapted to communicate a processed image of the subject 16 (e.g., 3D, semi-transparent rendering, and 2D slices through the 3D structure). With this variation, the probe display 60 is preferably adapted to display the processed image. In a third variation, the console transmitter 22 and the probe receiver 34 are adapted to communicate both the information about the system configuration and the processed images. With this variation, the handheld probe 14 may include an additional probe display 60, or may include a switch between the two sources. The probe display 60 preferably includes a conventional LCD screen, but may alternatively include any appropriate device such as individual lights, digital displays, alphanumeric displays, or other suitable indicators. With the probe controls 58 and the probe display 60, the handheld probe 14 of the preferred embodiment further exceeds the need to allow operation of an ultrasound system 10 during a patient examination without requiring physical proximity to the central console 12.

Figure 8:
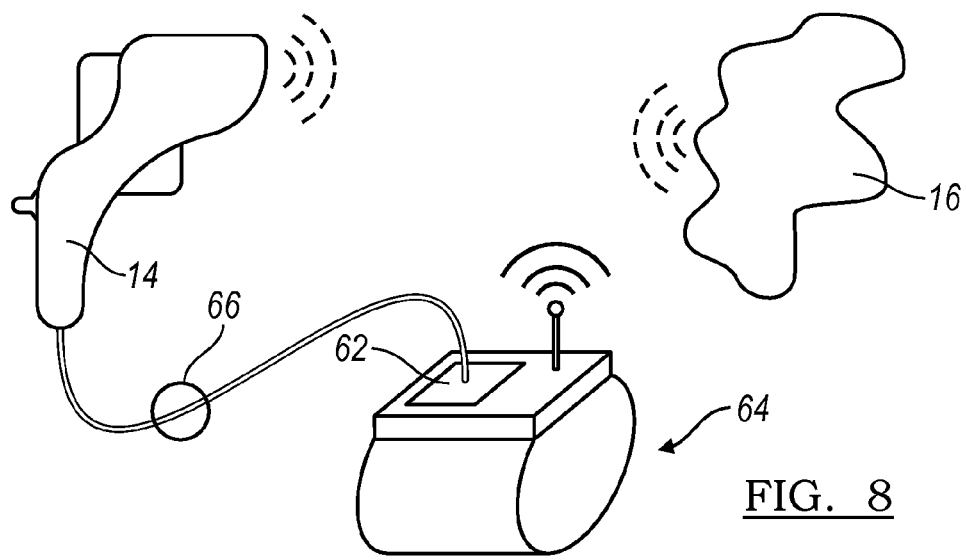
FIG. 8 is a representation of an alternative handheld probe for the ultrasound system.

In the preferred embodiment, the handheld probe 14 further includes a power source 62, which functions to power the components of the handheld probe 14. The power source 62 is preferably a conventional rechargeable battery, but may alternatively be a capacitor, a fuel cell, or any other suitable power source 62. Considering the state of battery technology, however, it is possible that the addition of a power source 62 would make the handheld probe 14 unacceptably heavy or bulky. Thus, in a variation of the preferred embodiment shown in FIG. 8, the power source 62 is located in a remote portion 64 of the handheld probe 14, which is connected to the handheld probe 14 with a lightweight cord 66. The remote portion 64 may be designed to be strapped to the operator's body (e.g., wrist, arm, or shoulder) or clipped to the operator's belt, with the cable routed such that it is kept conveniently out of the way (e.g., along the arm). Although this variation still requires a cable connected to the handheld probe 14, the cable moves with the operator and thus provides a degree of freedom that is still greater than a transducer head tethered to the central console. Further, in the variation of the preferred embodiment, other elements of the handheld probe 14 may be located in the remote portion 64. For example, the probe receiver, the probe transmitter, the probe controls, and/or the probe display may be located in the remote portion 64 of the handheld probe 14.

3. Structure of the First Integrated Circuit/Transducer Device

As shown in FIGS. 9, 10, 12, and 13, the first integrated circuit/transducer device 36 of the handheld probe includes both CMOS circuits 110 and cMUT elements 112. The cMUT elements 112 function to generate an ultrasonic beam, detect an ultrasonic echo, and output electrical signals, while the CMOS circuits 110 function to perform analog or digital operations on the electrical signals generated through operation of the cMUT elements 112. The first integrated circuit/transducer device 36 may be configured in any suitable size and shape, and may include any suitable number of CMOS circuits 110 and cMUT elements 112. Both the CMOS circuits 110 and cMUT elements 112 are preferably fabricated on a suitable substrate 113.

The CMOS circuits 110 function to perform analog or digital operations, such as multiplexing or amplification, on the electrical signals generated through operation of the cMUT elements 112. The CMOS circuits 110 preferably include any suitable number of p-type, n-type, and insulating dielectric layers, arranged into active and/or passivation layers, as well as electrical leads for receiving input signals, receiving electrical power, and transmitting output signals. The CMOS circuits 110 may, however, include any suitable layer, element, or object in a conventional complementary-metal-oxide-semiconductor process.

The cMUT elements 112 function to generate an ultrasonic beam, detect an ultrasonic echo, and output electrical signals. The cMUT elements 112 include at least one dielectric layer 114, a lower electrode 116, an upper electrode 118, and a cavity 120.

The dielectric layer 114 of the preferred embodiment functions to electrically and chemically isolate the lower electrode 116 and the upper electrode 118, and is accordingly preferably located between the lower electrode 116 and the upper electrode 118. The dielectric layer 114 preferably includes silicon dioxide or silicon nitride, but may alternatively include other suitable dielectric material usable in forming CMOS or MOS structures. The thickness of the dielectric layer can range between 0.5 microns and 1.5 microns, depending upon the functionality desired for the cMUT element 112.

Figure 9:
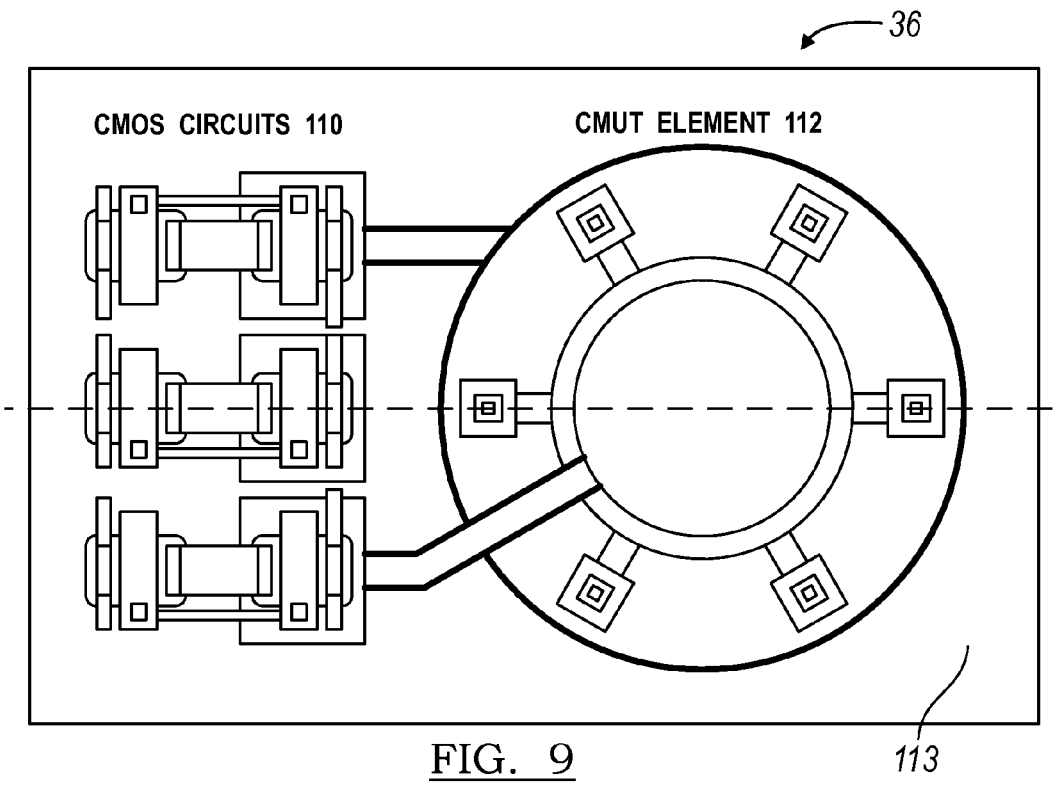
FIGS. 9 and 10 are top and side views, respectively, of the first integrated circuit/transducer device of the preferred embodiment.
Figure 10:
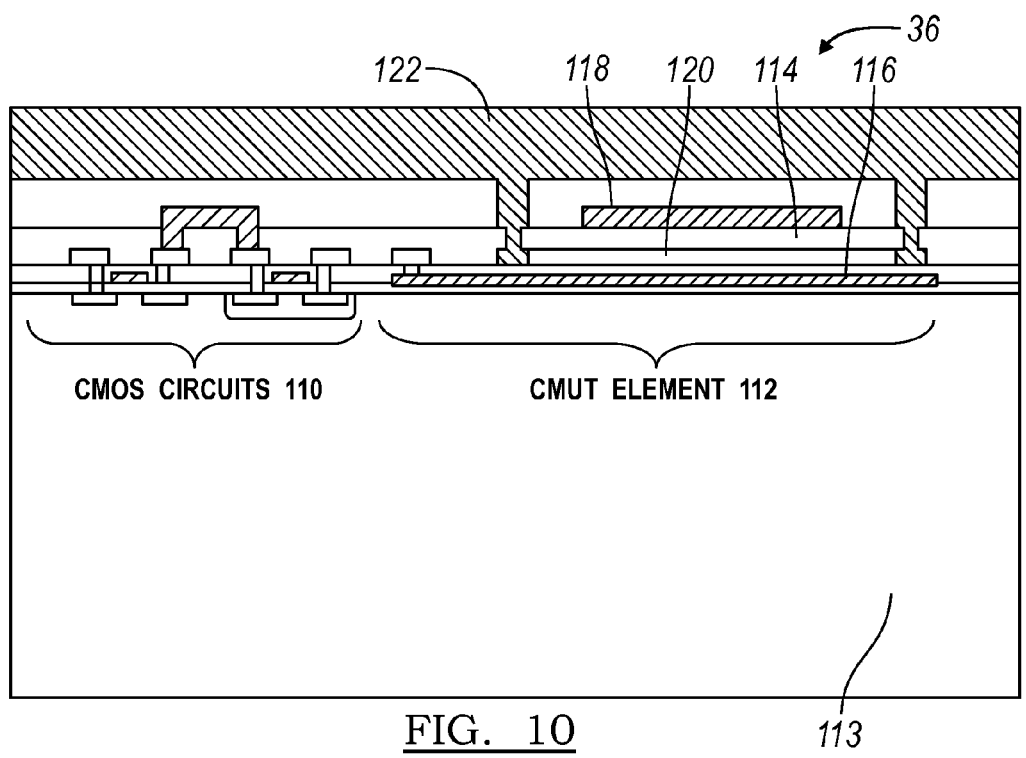
Figure 11:
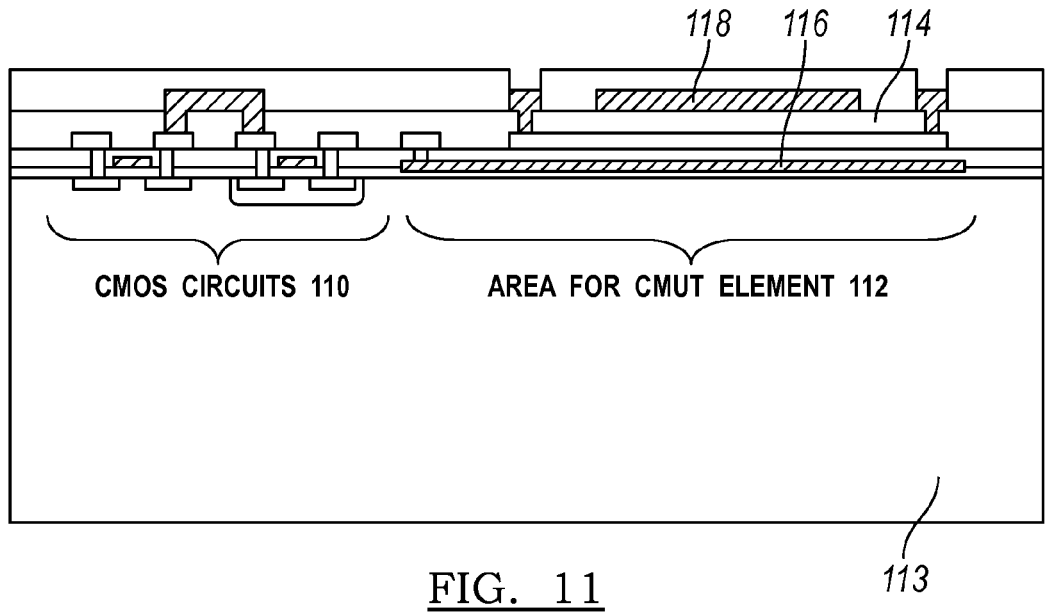
FIG. 11 is a side view of the first integrated circuit/transducer device of the preferred embodiment, shown in the first stage of the preferred manufacturing method.
Figure 12:
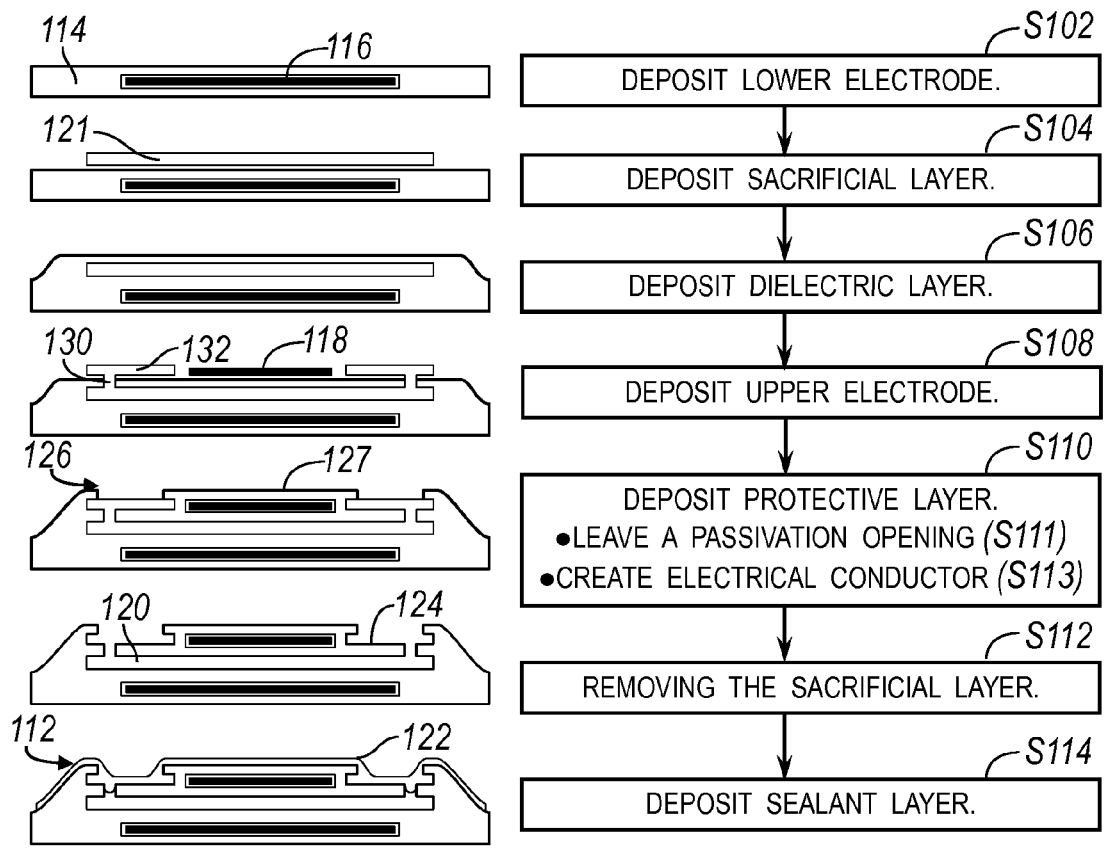
FIG. 12 is a flowchart depicting a manufacturing method of a capacitive micromachined ultrasonic transducer in accordance with the preferred manufacturing method.
Figure 13:
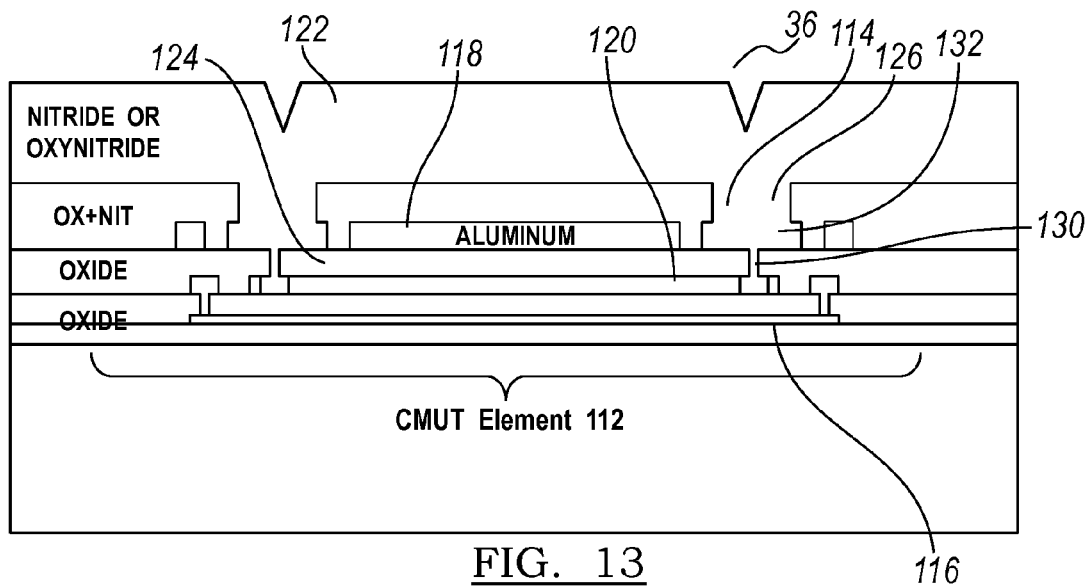
FIG. 13 is a side view of the second integrated circuit/transducer device of the preferred embodiment, shown in the final stage of the preferred manufacturing method.

The lower electrode 116 of the preferred embodiment functions to maintain a first electrical potential. To maintain a first electrical potential, the lower electrode is preferably connected to a power source that provides the necessary voltage. The lower electrode 116 preferably forms a layer within the CMOS circuits 110, and as such can function as a transistor gate, capacitor plate, metallization, or other layer. The lower electrode 116 further functions to provide one portion of a capacitor within the structure of the cMUT elements 112. The lower electrode 116 may be composed of any suitable material, including both metals and semiconductors, that is capable of maintaining a predetermined voltage level. In one variation, as shown in FIG. 9, the lower electrode 116 is doped polysilicon. In another variation, the lower electrode 116 is a metal. In both variations, the lower electrode 116 is preferably deposited by conventional methods, but may be deposited by any other suitable method.

The upper electrode 118 of the preferred embodiment functions to maintain a second electrical potential. To maintain a second electrical potential, the upper electrode 118 may be connected to a power source that provides the necessary voltage. The upper electrode 118 preferably forms a layer within the CMOS circuits 110, and as such can function as a transistor gate, capacitor plate, metallization, or other layer. The upper electrode 118 further functions to provide one portion of a capacitor within the structure of the cMUT elements 112. The upper electrode 118 may be composed of any suitable material, including both metals and semiconductors, that is capable of maintaining a predetermined voltage level. The upper electrode 118 is preferably deposited by conventional methods, but may be deposited by any other suitable method.

The system of the preferred embodiment additionally includes a membrane structure 124 that functions to structurally support the upper electrode 118 and allow for diaphragm-like motion. The membrane structure 124 preferably surrounds the whole upper electrode 118. The membrane structure 124 and the supported upper electrode 118 preferably act similar to a diaphragm, experiencing substantial deflection in response to electrostatic forces applied on the device and/or in response to an ultrasonic acoustic wave or any suitable force. The membrane structure 124 is preferably sufficiently flexible. The membrane 124 along the outer region (the rim) is preferably thinner than the central region of the membrane (where the upper electrode is preferably located). A passivation opening and/or sacrificial opening may additionally be used to create a thin membrane profile along the outer region of the membrane structure 124. The passivation opening and/or sacrificial opening are preferably ring shaped or any suitable shape substantially along the outer perimeter of the membrane structure 124. The membrane is, however, preferably thick enough to not collapse or degrade under DC and/or transient forces. A thin membrane structure 124 to upper electrode 118 thickness ratio may alternatively be used to allow for a more flexible diaphragm and increased sensitivity-bandwidth. The membrane structure 124 may alternatively be made with any suitable size. The membrane structure is preferably made from a dielectric layer as described above, but may alternatively be made from any suitable CMOS compatible layer or combination of layers. In one additional alternative, a sealant material also covers a dielectric layer to form the membrane structure 124. The membrane structure is preferably circularly shaped, but may alternatively be square shaped, uniformly shaped, non-uniformly shaped, or any suitable shape.

Additionally or alternatively, the preferred embodiment includes a passivation opening 126 defined in an upper passivation or overglass layer 127 that functions to promote the manufacturing of a membrane structure 124 with a thin profile. The passivation opening 126 preferably allows for the removal of sacrificial material in the form of a sacrificial ring, but the passivation opening 126 may alternatively be the only difference in thickness between the membrane structure 124 and the central region of the membrane that includes the upper electrode 118 layer.

Additionally or alternatively, the preferred embodiment includes a sacrificial opening 132 that functions as a manufacturing artifact causing the membrane structure 124 to be more flexible, preferably due to the thin section of the membrane structure defined within the region along the sacrificial opening 132. The sacrificial opening preferably causes the membrane structure 124 to be thinner than regions not aligned with the sacrificial opening 132 (such as the central region of the membrane where the upper electrode 118 is located). The sacrificial opening 132 is preferably a volume defined by surfaces of a dielectric layer 127. The sacrificial opening 132 is preferably located directly above a dielectric layer 127 of the membrane structure 124. The sacrificial opening 132 is preferably created by removing a ring of sacrificial material. The sacrificial material preferably acts as a buffer or filler material during the manufacturing process. The volume of the sacrificial opening 132 additionally may be filled with sealant material or any suitable material after the volume has been opened.

Figure 14:
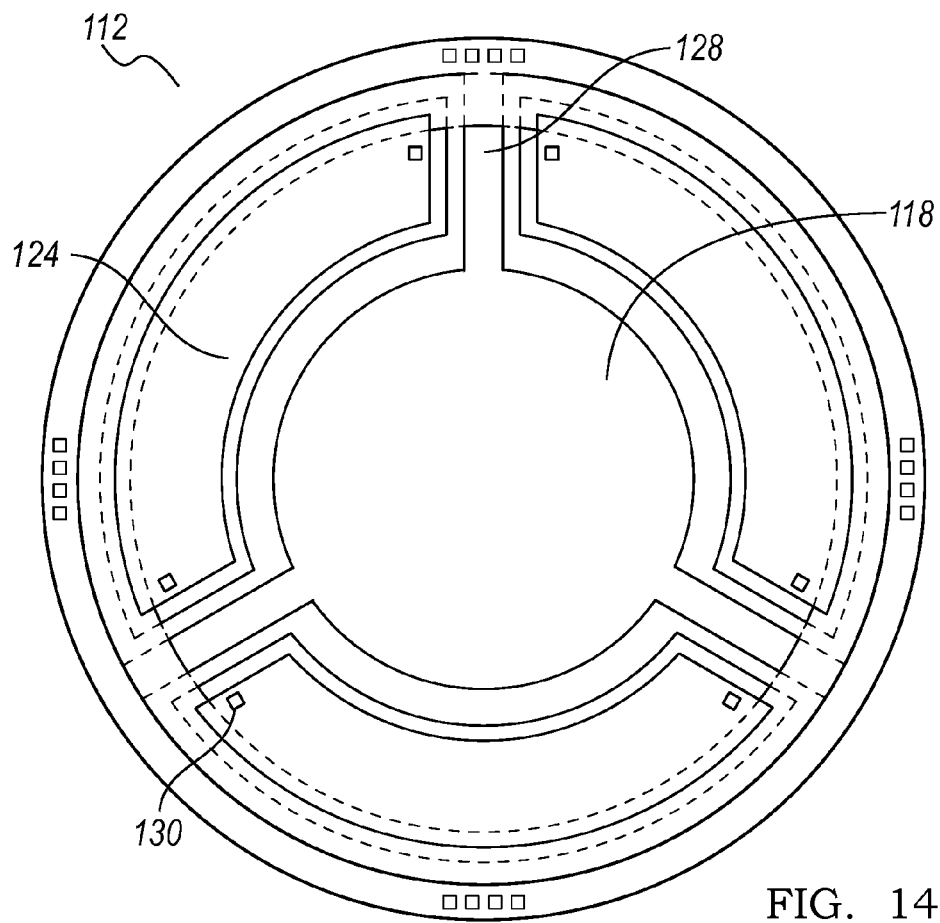
FIG. 14 is a top view of a preferred variation of the second integrated circuit/transducer device of the preferred embodiment.

As shown in FIG. 14, the cMUT may additionally include at least one electrical conductor 128 that functions to electrically connect the upper electrode 118 to another device such as the CMOS circuit 110. The electrical conductor 128 is preferably a flexible structure made out of a non-rigid conductor or alternatively, any suitable conductive material. However, the electrical conductor 128 is alternatively (and often out of necessity) a rigid conductive structure spanning across the membrane structure 124 to the upper electrode 118. The rigidity of the electrical conductor affects the mechanical properties of the membrane structure 124. Preferably, a plurality of electrical conductors 128 is symmetrically arranged around the upper electrode to provide mechanical symmetry to the diaphragm-like structure. In one example, three electrical conductors 128 are arranged 120 degrees apart, around the upper electrode 118. A single electrical conductor 128 may alternatively be used to minimize the added rigidity to the membrane structure 124. Alternatively, any suitable number of electrical conductors in any suitable arrangement may be used.

The cavity 120 of the preferred embodiment, which is formed between the lower electrode 116 and the upper electrode 118, functions to facilitate relative displacement of the lower electrode 116 and the upper electrode 118, which thereby allow the cMUT elements 112 to receive and transmit acoustic waves, preferably at ultrasonic frequencies. The cavity 120 further functions to provide an air or vacuum gap capacitor formed by its position relative to the lower electrode 116 and the upper electrode 118. As acoustic waves are directed towards the cavity 120, the transmission of those waves will cause relative displacement of the upper electrode 118 and the lower electrode 116, which in turn will cause a change in the capacitance between the upper electrode 118 and the lower electrode 116. The cavity 120 may be of any suitable dimension for use in the acoustic detection arts, depending upon the application and the frequencies of the transmitted and received waves. The cavity 120 preferably has a depth of 0.1 microns to 1.5 microns and lateral dimensions of 10 microns to 1 millimeter, depending upon the application for which the first integrated circuit/transducer device 36 is designed. The cavity 120 is preferably created by removing a sacrificial layer 121 from a volume between the upper electrode 118 and the lower electrode 116. The sacrificial layer removal process is preferably facilitated by etch ports 130. Etch ports are preferably etched openings leading to the sacrificial layer. Though, any suitable manufacturing steps may alternatively be used to create the cavity 120.

The cMUT element 112 preferably includes etch ports 130 that function to facilitate the creation of the cavity 120. The cMUT element 112 preferably includes at least one etch port 130, and preferably includes a plurality of etch ports 130. Preferably, the etch ports 130 are positioned near the outer perimeter of the membrane structure 124 near the electrical conductors 128. By positioning the etch ports near an electrical conductor 128, any sealant material that happens to leak into the cavity will preferably have a minimal effect on the mechanical properties of the diaphragm-like structure because the rigidity of the electrical conductor 128 will dominate the mechanics of that area. Additionally, positioning the etch ports along the outer perimeter of the membrane structure 124 preferably minimizes the effects of possible sealant material in the cavity since the membrane is preferably anchored to the substrate around the perimeter by design. Additionally, positioning the etch ports within the perimeter of the membrane reduces the footprint of the cMUT element 112. Alternatively, any suitable positioning or arrangement of the etch ports 130 may be used.

The first integrated circuit/transducer 36 of the preferred embodiment also includes a sealant layer 122 disposed on the cMUT elements 112. The sealant layer 122 functions to prevent fluid, air, or debris from entering the cavity 120 and impeding relative displacement of the lower electrode 116 and the upper electrode 118 during acoustic transmission or reception. The sealant layer 122 may be any suitable material used in the art of semiconductor manufacturing and micromachining, including for example silicon dioxide, silicon nitride, or a mixture of the two (referred to as "oxynitride"). The sealant layer 122 may alternatively be a vacuum-deposited polymer such as parylene, or it may be a thin flexible membrane material applied as a sheet adhered to the dielectric layer 114 by chemical or thermal activation. The sealant layer 122 additionally may form a layer of the membrane structure 124. The sealant layer 122 is preferably impermeable to air and water or similar fluids. The sealant layer 122 is also preferably mechanically flexible so as to minimally impede displacement of the relative displacement of the lower electrode 116 and the upper electrode 118 during acoustic transmission or reception.

4. Method of Manufacturing the First Integrated Circuit/Transducer Device

The mechanical structure of the first integrated circuit/transducer device 36 is preferably formed by layers deposited and patterned as part the foundry CMOS process itself (and preferably not augmented with additional steps for depositing material and aligning/patterning layers). The steps performed on the first integrated circuit/transducer device 36 after the foundry fabrication preferably include only blanket etch and deposition steps, which require no alignment procedure or only rough alignment (with tolerances greater than 400 µm).

As described above, the first integrated circuit/transducer device 36 consists of a lower electrode, a dielectric layer, and an upper electrode, with all layers integral to the CMOS process flow. In summary, a capacitive gap with a thickness of 0.1 microns to 1.5 microns is preferably formed by selectively etching a sacrificial metal layer (also integral to the CMOS process) that has been patterned to be exposed when the chip is immersed in a metal etch solution after completion of the foundry CMOS process. A vacuum-sealed cavity is preferably formed between the membrane and the lower electrode by sealing access ports to the gap using a low-temperature blanket dielectric deposition under vacuum (by PECVD and/or sputtering). More details of the process appear below.

As shown in FIGS. 11-14, the manufacturing method for the first integrated circuit/transducer device 36 of the preferred embodiment includes the steps of depositing the lower electrode S102; depositing a sacrificial layer S104; depositing a dielectric layer S106; depositing the upper electrode S108; depositing a protective layer on the upper electrode S110; and removing the sacrificial layer S112. In the preferred embodiment, the manufacturing method also includes the step of depositing a sealant layer to seal a cavity between the lower electrode and the upper electrode S114.

Step S102 of the preferred method, which includes depositing the lower electrode, functions to create a first layer to maintain an electric potential. The lower electrode is also preferably connected to the CMOS circuit to form an electrical connection. The lower electrode layer is preferably composed of suitable material, including both metals and semiconductors, that are capable of maintaining a predetermined voltage. In one variation, the lower electrode is doped polysilicon. In another variation, the lower electrode is a metal. The lower electrode is preferably deposited by conventional means, but may alternatively be deposited by any suitable method.

Step S104 of the preferred method, which includes depositing a sacrificial layer, functions to create a buffer of material to later create a cavity. The sacrificial layer, which is deposited over the lower electrode, is removed at a later step in the preferred method. The sacrificial layer functions to create a volume of space between the lower electrode and the upper electrode, which is subsequently evacuated to form the cavity. The sacrificial layer may be deposited directly on the lower electrode, or may be deposited on the dielectric layer, which is deposited directly on the lower electrode. As described above, the cavity may be of any suitable dimension for use in the acoustic detection arts, depending upon the application and the frequencies of the transmitted and received waves. Accordingly, the sacrificial layer deposited over the lower electrode preferably has a thickness that is substantially identical to the depth sought for the cavity, such as a thickness of approximately 0.1 microns to approximately 1.5 microns. The sacrificial layer may be any suitable material that is distinct from the dielectric layer, such that the sacrificial layer—and not the dielectric material—is removed during the process of removing the sacrificial layer.

Step S106 of the preferred method, which includes depositing a dielectric material functions to electrically and chemically isolate the lower electrode and the upper electrode. The dielectric material additionally functions as the base of the membrane structure or a portion of the membrane structure. The dielectric material is preferably deposited between the lower electrode and the upper electrode. The dielectric material is preferably deposited on top of the sacrificial layer, and may additionally be deposited as any suitable layer. The dielectric layer 114 preferably includes silicon dioxide or silicon nitride, but may alternatively include other suitable dielectric material usable in forming CMOS or MOS structures. The thickness of the dielectric layer can range between 0.5 microns and 1.5 microns, depending upon the functionality desired for the cMUT element 112.

Step S108 of the preferred method, which includes depositing the upper electrode over the membrane material, functions to create an upper electrode to maintain a second electrical potential. The upper electrode, in this variation, functions to provide one portion of a capacitor within the structure of the CMOS integrated circuit. As shown in FIG. 14, the upper electrode is preferably smaller than the lower electrode and preferably structurally supported by a membrane structure. Electrical conductors may additionally span the membrane structure to connect to the upper electrode. The electrical conductors preferably form an electrical connection from the upper electrode to an outside circuit such as the CMOS circuit.

Step S110 of the preferred method, which includes depositing a protective layer over the upper electrode, functions to isolate and protect the upper electrode. The protective layer preferably includes any suitable material that is electrically distinct from the upper electrode, including both dielectric materials and sealant layers. The protective layer functions to electrically isolate the upper electrode and to protect the upper electrode from unwanted debris and environmental interference with the operation of the cMUT device. Additionally, Step S110 includes a sub-step of leaving an opening that substantially encircles the upper electrode S111. The opening is preferably an opening in a passivation layer, but the opening may be any suitable opening. The opening functions to promote the manufacturing of a membrane structure with a flexible and thin profile. The opening is preferably a volume with a thinner or no protective layer. As an additional alternative, a sacrificial opening may be created in approximately the same location. The sacrificial opening is preferably made to satisfy a CMOS manufacturing design rule that states a passivation opening must occur only above a metal layer. The sacrificial opening is used to create the opening without adding rigidity to the membrane structure. Other design rules may alternatively not necessitate a sacrificial opening. The material of the sacrificial opening is preferably substantially similar to the sacrificial layer, and is preferably removed when the sacrificial layer is removed, but may be made from any suitable material. The opening is preferably filled, partially filled, supported, and/or located above the sacrificial opening. The opening and the sacrificial opening both function to create a membrane structure with non-uniform thickness that engenders flexibility in the structure. The regions of the opening and sacrificial opening are preferably thinner than the central region of the membrane structure 124 near the upper electrode layer Step S112 of the preferred method recites removing the sacrificial layer. Preferably a portion of the upper electrode deposition layer is removed simultaneously with the sacrificial layer. As noted above, step S112 is preferably performed subsequent to steps S102 through S110. Removal of the sacrificial layer results in the formation of the cavity, with an air or vacuum gap, between the upper electrode and the lower electrode, and additionally a membrane structure is also created to support the upper electrode. The removal of the sacrificial layer may additionally open the sacrificial opening. The removal of the sacrificial layer is preferably accomplished with any known or suitable process for removing materials used in semiconductor manufacturing. The selected removing mechanism depends largely upon the type of sacrificial material used, and can be readily selected by those skilled in the art of semiconductor manufacturing. For example, if the sacrificial material is aluminum, then the step of removing the sacrificial layer can include etching in a phosphoric/nitric/acetic acid solution such as Aluminum Etch A, from Transene, Inc.

Step S114 of the preferred embodiment, which includes depositing a sealant layer to seal a cavity between the lower electrode and the upper electrode, functions to protect the cMUT device and prevent fluid, air, or debris from entering the cavity. The sealant layer may be any suitable material used in the art of semiconductor manufacturing and micromachining, including for example silicon dioxide, silicon nitride, or a mixture of the two (referred to as "oxynitride"). The sealant layer may alternatively be a vacuum-deposited polymer such as parylene, or it may be a thin flexible membrane material applied as a sheet adhered to the dielectric layer 114 by chemical or thermal activation. The sealant layer additionally may form a layer of the membrane structure. The sealant layer is preferably impermeable to air and water or similar fluids. The sealant layer is also preferably mechanically flexible so as to minimally impede displacement of the relative displacement of the lower electrode and the upper electrode during acoustic transmission or reception.

Additionally, the preferred embodiment includes the step of creating at least one electrical conductor that spans the membrane structure and connects to the upper electrode S113. Step S113 functions to create an electrical interconnect for the upper electrode. The electrical conductor is preferably made of conductive material. The electrical conductor is preferably a flexible conductor, but alternatively (and often) the electrical conductor is a rigid structure and thus creates a stiffer diaphragm-like structure. The affects of creating an electrical conductor are preferably accounted for in the cMUT design. A plurality of electrical conductors is preferably arranged symmetrically around the upper electrode to create a mechanically symmetric device. A single electrical conductor or an asymmetric arrangement of electrical conductors may alternatively be used.

As an addition to the preferred embodiment, the method may include etching the sacrificial layer using at least one etch port along the membrane perimeter and near an electrical connector S111. Step S111 functions to minimize the effect of an etch port on the mechanical properties of the device and additionally, reduce the footprint of the cMUT device (so that more cMUT elements may be arranged closer together). The etch ports preferably lead from an open surface (the top surface) to the sacrificial layer. Alternatively, the etch ports may be covered by a layer of other sacrificial material such as at the sacrificial opening. The sacrificial layer is preferably accessed via the etch ports. Sealant material may leak through the etch ports during Step S114, but preferably the mechanical properties of the cMUT are not altered much because the proximity of an electrical conductor and the anchored membrane perimeter is substantially near the etch port. The etch ports may alternatively be positioned and sized in any suitable fashion.

In an alternative embodiment, Steps S104 and S112 may be altered to use other suitable materials. For example, Steps S104 may include depositing a polysilicon layer (also integral to the CMOS process flow) as the sacrificial layer. Etch ports to the polysilicon layer are preferably opened by immersing the chip in a metal etch solution to expose metal-polysilicon contact holes. The polysilicon sacrificial layer is preferably etched with a wet or dry isotropic etchant such as xenon difluoride gas using an apparatus such as that described in U.S. Pat. No. 6,887,337, which is hereby incorporated in its entirety by this reference. A vacuum-sealed cavity is then formed between the membrane and the lower electrode by sealing access ports to the gap using a low-temperature blanket dielectric deposition under vacuum (by PECVD, sputtering, parylene deposition, or any other suitable method).

As a person skilled in the art of ultrasound systems will recognize from the previous detailed description and from the figures and claims, modifications and changes can be made to the preferred embodiment of the invention without departing from the scope of this invention defined in the following claims.

We claim:

1. An integrated circuit/transducer device, comprising:
   a substrate;
   a complementary-metal-oxide-semiconductor (CMOS) circuit fabricated on the substrate; and
   a capacitive micromachined ultrasonic transducer (cMUT) element fabricated on the substrate and connected to the CMOS circuit, wherein the CMOS circuit and the cMUT element are fabricated during the same foundry process, and wherein the cMUT element includes:
      a lower electrode adapted to maintain a first electrical potential,
      an upper electrode adapted to maintain a second electrical potential,
      a membrane structure that structurally supports the upper electrode over the lower electrode, wherein an outer region of the membrane structure is thinner than a central region of the membrane, and
      a cavity between the lower electrode and the upper electrode, wherein the lower electrode and the upper electrode of the cMUT each form a layer of the CMOS circuit.

2. An integrated circuit/transducer device, comprising:
   a substrate;
   a complementary-metal-oxide-semiconductor (CMOS) circuit fabricated on the substrate; and
   a capacitive micromachined ultrasonic transducer (cMUT) element fabricated on the substrate and connected to the CMOS circuit, wherein the CMOS circuit and the cMUT element are fabricated during the same foundry process, and wherein the cMUT element includes:
      a lower electrode adapted to maintain a first electrical potential,
      an upper electrode adapted to maintain a second electrical potential,
      a membrane structure that structurally supports the upper electrode over the lower electrode, wherein an outer region of the membrane structure is thinner than a central region of the membrane,
      a cavity between the lower electrode and the upper electrode, and
      at least one electrical conductor spanning the membrane and connected to the upper electrode.

3. The device of claim 2 wherein a plurality of electrical conductors connecting the upper electrode to the CMOS circuit are arranged to achieve symmetric mechanical rigidity.

4. The device of claim 3 wherein three electrical conductors are arranged radially and equally spaced around the upper electrode that is circularly shaped.

5. The device of claim 2 wherein a passivation opening is defined above a portion of the surface of the membrane.

6. The device of claim 5 further including at least one etch port that promotes the removal of a sacrificial layer to create the cavity, wherein the etch port is positioned along the membrane perimeter substantially near an electrical conductor.

7. The device of claim 6 wherein the lower electrode is metal.

8. The device of claim 6 wherein the lower electrode is polysilicon.

9. The device of claim 6 wherein the upper electrode is disposed within the dielectric layer and the membrane structure is composed of the dielectric layer.

10. The device of claim 6 further comprising a sealant layer disposed on the dielectric layer wherein the sealant layer seals the cavity.

11. The device of claim 10 wherein the sealant is parylene.

* * * * *